United States Patent
Riisager et al.

(10) Patent No.: US 8,003,822 B2
(45) Date of Patent: Aug. 23, 2011

(54) PROCESS FOR CONTINUOUS CARBONYLATION BY SUPPORTED IONIC LIQUID-PHASE CATALYSIS

(75) Inventors: Anders Riisager, Taastrup (DK); Rasmus Fehrmann, Copenhagen Ø (DK)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/920,691

(22) PCT Filed: May 19, 2006

(86) PCT No.: PCT/DK2006/000275
§ 371 (c)(1),
(2), (4) Date: Jan. 17, 2008

(87) PCT Pub. No.: WO2006/122563
PCT Pub. Date: Nov. 23, 2006

(65) Prior Publication Data
US 2009/0030229 A1    Jan. 29, 2009

(30) Foreign Application Priority Data

May 20, 2005 (DK) ................................. 2005 00735

(51) Int. Cl.
*C07C 53/08* (2006.01)
(52) U.S. Cl. ......................................................... 562/607
(58) Field of Classification Search .................. None
See application file for complete search history.

(56) References Cited

U.S. PATENT DOCUMENTS

| | | | |
|---|---|---|---|
| 3,769,329 A | 10/1973 | Paulik et al. | |
| 4,366,259 A | 12/1982 | Knifton et al. | |
| 5,001,259 A | 3/1991 | Smith et al. | |
| 6,617,471 B2* | 9/2003 | Zoeller et al. | 560/232 |
| 2003/0212295 A1* | 11/2003 | Charles et al. | 562/518 |
| 2004/0059153 A1 | 3/2004 | Magna et al. | |

FOREIGN PATENT DOCUMENTS

| | | |
|---|---|---|
| WO | 01/07388 A1 | 2/2001 |
| WO | WO 01/07388 A1 | 2/2001 |

OTHER PUBLICATIONS

Mehnert, C P., "Supported Ionic Liquid Catalysis" Chemistry—A European Journal, vol. II, pp. 50-56, Jan. 2005.*
Abstract, Zhang et al., Cuihua Xuebao (2004), 25(8), 607-610 (CAS online citation 142:373529 [retrieved Feb. 4, 2009] from STN; Columbus, OH, USA.*
XP-002371152: Mehnert, C.P., "Supported Ionic Liquid Catalysis", Chemistry—A European Journal, vol. 11, pp. 50-56, (Jan. 2005).
"Cunning Catalyst controls Cativa", Process Engineering, p. 21, (Jul./Aug. 1996).
Process Engineering, Jul./Aug. 1996, p. 21.
Mehnert, Christian P., "Supported Ionic Liquid Catalysis," Chemistry—A European Journal, Jan. 2005, pp. 50-56, vol. 11, Wiley-VCH Verlag GmbH & Co. KGaA, Weinheim, Germany.

* cited by examiner

*Primary Examiner* — Karl J Puttlitz
(74) *Attorney, Agent, or Firm* — The Nath Law Group; Tanya E. Harkins; Ari G. Zytcer

(57) ABSTRACT

A process for continuous carbonylation of carbonylatable reactants with carbon monoxide in the gaseous phase in the presence of a catalyst, wherein said catalyst is a Supported Ionic Liquid-Phase (SILP) catalyst comprising a solution of a Group VIII metal in an ionic liquid confined on a support. The SILP catalyst offers a very large active catalyst area resulting in a very efficient use of catalyst material and a simple apparatus design.

22 Claims, 1 Drawing Sheet

PROCESS FOR CONTINUOUS CARBONYLATION BY SUPPORTED IONIC LIQUID-PHASE CATALYSIS

TECHNICAL FIELD

The present invention relates to a process for continuous carbonylation of carbonylatable reactants with carbon monoxide in the gaseous phase in the presence of a catalyst, wherein said catalyst is a Supported Ionic Liquid-Phase (SILP) catalyst comprising a solution of a Group VIII metal in an ionic liquid confined on a support.

BACKGROUND ART

Carbonylation of carbonylatable reactants, especially alcohols, in particular methanol, is an industrially important homogeneous catalysed batch reaction. Processes for the manufacture of acetic acid from methanol by carbonylation are operated extensively throughout the world. Acetic acid is used in a variety of applications, among which are in the manufacture of (poly) vinyl acetate, cellulose acetate, acetic anhydride, and acetyl chloride.

The manufacture of acetic acid from methanol and carbon monoxide at high temperature and high pressure was described by BASF as early as 1913. In 1941 BASF developed an improved process using Group VIII metal carbonyls as catalysts for carbonylation reactions. This led to the development of a high-pressure, high-temperature process (70 MPa, 250° C.) with a cobalt iodide catalyst.

Monsanto developed a low-pressure process for the manufacture of acetic acid in the late 1960s with a rhodium iodide promoted catalyst system that demonstrated a pronounced higher selectivity and activity than the cobalt-based process, U.S. Pat. No. 3,769,329. The Monsanto operating conditions in the reactor were milder (3-4 MPa and 180-220° C.) than in the BASF process.

In the early 1980s Celanese Chemical Company developed a low-reaction-water rhodium -catalysed methanol carbonylation process using inorganic iodide salts to improve catalyst stability and activity, U.S. Pat. No. 5,001,259.

BP developed in the early 1990s a process using iridium instead of rhodium in the catalyst system, a process known as the Cativa™ process (Process Engineering, 1996, July, p. 21). Said process is claimed to improve catalyst stability, increase reaction rates, increase yields, and produce less liquid by-products.

Thomas Swan & Co. discloses in WO 01/07388 a continuous process for carrying out carbonylation reactions with carbon monoxide using a heterogeneous catalyst with or without use of a solvent medium, wherein at least one component is under supercritical or near critical conditions.

Ionic liquids have been used as solvents for organic reactions and metal-catalysed reactions including carbonylation reactions.

US 2004/0059153 (Institut Francais du Petrole) discloses a process for liquid phase carbonylation of alcohols by carbon monoxide in the presence of at least one catalyst comprising at least one rhodium and/or iridium complex and a halogenated promoter in at least one non-aqueous ionic liquid. The liquid product of the process must be separated by distillation after decreasing the pressure. Said decrease in pressure may cause more or less pronounced deactivation of the catalyst system used.

U.S. Pat. No. 4,366,259 discloses a high pressure batch process for preparing acetic acid and propionic acid and their esters by contacting a mixture of carbon monoxide and hydrogen gas with a catalyst system comprising a ruthenium-containing compound and a cobalt halide dispersed in a low melting quaternary phosphonium or ammonium base or salt. The liquid product must be separated by distillation.

The liquid phase processes discussed above require separation of the reaction products from the catalysts by distillation from the reactor or by flashing of the reaction solution at reduced pressure. Catalyst decomposition and precipitation may cause problems during the flashing process wherein the liquid products from the reactor are sub-jected to a pressure decrease. Furthermore these separation processes are often cumbersome, require additional reaction steps, and require the use of expensive corrosion-resistant equipment..

US 2003/0212295 (Charles et al.) discloses a continuous process for the preparation of carbonylatable products wherein carbon monoxide, a reactant and a halide in the gas phase are contacted with a non-volatile catalyst solution comprising an ionic liquid and a Group VIII metal to produce a carbonylation product in the gas phase. The process is said to be useful for the continuous preparation of acetic acid by the carbonylation of methanol. The catalytically active component is incorporated in the ionic liquid, which is positioned in the reactor on a metal filter.

A need still exists for an improved process for the carbonylation of carbonylatable reactants, which provides for use of less catalyst materials, presents few requirements for the equipment used and allows a simple process design without the need for recirculation of and pressure change for the catalyst system.

DISCLOSURE OF INVENTION

The present invention relates to a process for continuous carbonylation of carbonylatable reactants with carbon monoxide in the gaseous phase in the presence of a catalyst, wherein said catalyst is a Supported Ionic Liquid-Phase (SILP) catalyst comprising a solution of a Group VIII metal in an ionic liquid confined on a support.

The present invention thus describes a highly efficient carbonylation process. The use of a SILP catalyst provides a very large active catalyst area ensuring a very effective use of the catalyst. Since the catalyst is maintained in the carbonylation reactor the process according to the invention obviates the need for subsequent separation of any catalyst under decreased pressure with the concomitant deactivation and decomposition problems experienced with prior art carbonylation processes.

The present invention furthermore relates to an apparatus for carrying out the carbonylation process according to the invention characterised in that it comprises:
i) at least one reactor 1;
ii) at least one liquid evaporator 2;
iii) at least one condenser 3;
iv) at least one separator 4 to separate the product stream from residual process gas which is recycled to said at least one reactor.

Finally the present invention relates to the use of a SILP catalyst for use in the carbonylation process according to the invention.

BRIEF DESCRIPTION OF THE DRAWINGS

The invention is explained in detail below with reference to the drawing(s), in which.

BEST MODES FOR CARRYING OUT THE INVENTION

Figure 1:
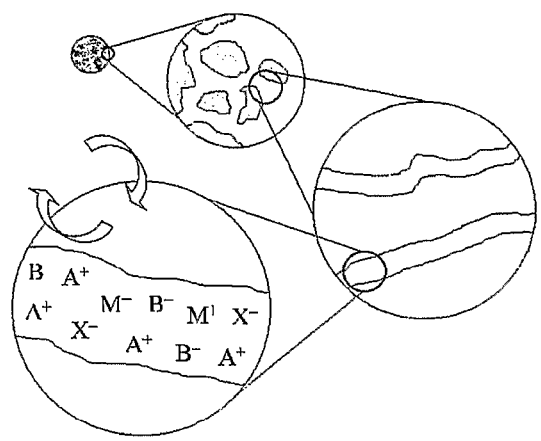
FIG. 1 shows schematically the build-up of a SILP catalyst particle.

More particularly the present invention relates to a process for carbonylation of carbonylatable reactants, comprising:

i) continuously feeding to a reaction zone a carbonylatable reactant and carbon monoxide, wherein said carbonylatable reactant and carbon monoxide are in the gaseous phase;
ii) continuously contacting said carbonylatable reactant and carbon monoxide with a SILP catalyst comprising a solution of a Group VIII metal in an ionic liquid confined on a support; and
iii) continuously recovering from said reaction zone a gaseous effluent comprising a carbonylated product.

Although a carbonylation reaction may be performed simply as a reaction between a carbonylatable reactant and carbon monoxide it has been shown that an enhanced yield and selectivity may be obtained by the addition of a reaction promoter. Consequently in a preferred embodiment of the continuous process according to the invention a reaction promoter is added to the liquid feed initially and re-circulated by the residual process gas. A reaction promoter may act as a (co)-catalyst and is not consumed once steady-state conditions have been reached.

The Group VIII metal of the SILP catalyst used in the process according to the invention may be any Group VIII metal which will react with carbon monoxide in the reaction medium to produce a metal-carbonyl complex. Preferred Group VIII metals are selected from iron, ruthenium, rhodium, iridium, nickel, cobalt, palladium or any combinations thereof.

Any source of catalyst precursor which will liberate the Group VIII metal by dissolution in an ionic liquid may be used as Group VIII metal catalyst precursor. Examples of catalyst precursors include, without limitation, $Rh(CO)_2$(acac), $Rh(COD)(acac)$, $[Rh(COD)Cl]_2$, $[Rh(CO)_2Cl]_2$, $[Rh(CO)_2]_2$, $[Rh(OAc)_2]_2$, $RhCl_3 \cdot xH_2O$, $[Ir(COD)Cl]_2$, $Ir(CO)_2$(acac), $IrCl_3 \cdot xH_2O$, $Pd(OAc)_2$, $Pd(acac)_2$, $Co(acac)_2 \cdot xH_2O$, $[Ru(COD)Cl_2]_x$, wherein acac=acetylacetonate, OAc=acetate, and COD=1,5-cyclooctadiene.

Ionic liquids are liquids composed solely of ions. Ionic liquids are characterised by having a melting point below about 100° C. distinguishing ionic liquids from traditional molten salts. An advantage by using ionic liquids is their negligible vapour pressure below their point of decomposition. This allows the separation of mixtures of ionic liquid and volatile substances, which makes them suitable as solvents for organic reactions. Furthermore said fact means that ionic liquids are not lost by evaporation like common organic solvents.

The physical and chemical properties of ionic liquids may be adjusted by selection of the ions of the ion pair, which again allows the designing of an ionic liquid having the properties desired. Thus, the cation of an ionic liquid dictates to a large degree the melting point of said ionic liquid. Generally the bigger the cation the lower the melting point. Furthermore the degree of cation substitution influences the lipophilicity of an ionic liquid and thus the miscibility with an organic solvent. Preferred cations of the ionic liquids used in the SILP catalysts employed in the process according to the invention are quaternary nitrogen- and/or quaternary phosphorous-containing cations.

Particularly preferred cations of the ionic liquids are selected from the group consisting of

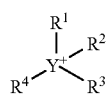

i)

wherein $R^1$, $R^2$, $R^3$, and $R^4$ are independently selected from optionally substituted, linear or branched-chained $C_1$-$C_{20}$ alkyl, optionally substituted cyclic $C_3$-$C_{20}$ alkyl, and optionally substituted $C_6$-$C_{20}$ aryl; and Y is N or P;

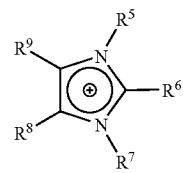

ii)

wherein $R^5$ and $R^7$ are independently selected from optionally substituted, linear or branched-chained $C_1$-$C_{20}$ alkyl, optionally substituted cyclic $C_3$-$C_{20}$ alkyl, and optionally substituted $C_6$-$C_{20}$ aryl; and
$R^6$, $R^8$ and $R^9$ are independently selected from hydrogen, optionally substituted, linear or branched-chained $C_1$-$C_{20}$ alkyl, optionally substituted cyclic $C_3$-$C_{20}$ alkyl, and optionally substituted $C_6$-$C_{20}$ aryl;

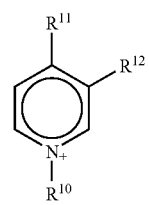

iii)

wherein $R^{10}$ is independently selected from optionally substituted, linear or branchedchained $C_1$-$C_{20}$ alkyl, optionally substituted cyclic $C_3$-$C_{20}$ alkyl, and optionally substituted $C_6$-$C_{20}$ aryl; and
$R^{11}$ and $R^{12}$ are independently selected from hydrogen, optionally substituted, linear or branched-chained $C_1$-$C_{20}$ alkyl, optionally substituted cyclic $C_3$-$C_{20}$ alkyl, and optionally substituted $C_6$-$C_{20}$ aryl; and

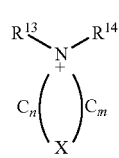

iv)

wherein $R^{13}$ and $R^{14}$ are independently selected from optionally substituted, linear or branched-chained $C_1$-$C_{20}$ alkyl, optionally substituted cyclic $C_3$-$C_{20}$ alkyl, and optionally substituted $C_6$-$C_{20}$ aryl; X is C, N, O, or S; n and m are each integers from 0 to 6 with the proviso that the sum $1 \leq m+n \leq 6$.

Non-limiting examples of alkyl moieties of the substituents mentioned above include methyl, ethyl, n-propyl, iso-propyl, cyclo-propyl, n-butyl, iso-butyl, sec-butyl, tert-butyl, npentyl, n-hexyl, cyclo-hexyl, n-octyl, and iso-octyl. Non-limiting examples of aryl groups include phenyl, benzyl, and ethyl-phenyl. As examples of substituents of the above alkyl and aryl groups may be mentioned, without limitation, halogen, such as fluoro, chloro, bromo or iodo, hydroxy, $C_1$-$C_6$ alkyl, and $C_1$-$C_6$ alkoxy.

The anion of an ionic liquid is generally considered to be the ion having the most profound influence on the water-solubility thereof. Thus a hydrophobic anion results in a poor water-solubility. Likewise water is poorly soluble in an ionic liquid comprising a hydrophobic anion. The viscosity of an ionic liquid depends largely on the anion, since the charge density on the anion may contribute to hydrogen bonds between the cation and the anion, the strength of hydrogen bonds being one of the significant causes of higher viscosity. Preferred anions of the ionic liquids are selected from the group consisting of halides, nitrates, sulfates, sulfonates, sulfonyl amides, phosphates, borates, antimonates, and acetates or optionally halogen substituted hydrocarbyl derivatives thereof.

Examples of preferred ionic liquids for employment in the SILP catalysts for use in the process according to the invention are selected from tetrabutylphosphonium tetrafluoroborate, N-butylpyridinium hexafluorophosphate, N-ethylpyridinium tetrafluoroborate, 1-butyl-1-methylpyrrolidinium bis(trifluoromethylsulfonyl)amide, 1-butyl-3-methylimidazolium tetrafluoroborate, 1-butyl-3-methylimidazolium hexafluorophosphate, 1-butyl-3-methylimidazolium trifluoromethylsulfonate, 1-butyl-3-methylimidazolium bis(trifluoromethylsulfonyl)amide, 1-ethyl-3-methylimidazolium bis(trifluoromethylsulfonyl)amide, 1-butyl-3-methylimidazolium acetate, 1-butyl-3-methylimidazolium iodide, 1-ethyl-3-methylimidazolium hydrogensulfate, 1-butyl-3-methylimidazolium methylsulfate, 1-ethyl-3-methylimidazolium ethylsulfate, 1-butyl-3-methylimidazolium octylsulfate, 1,3-dimethylimidazolium octylsulfate, 1-butyl-3-ethylimidazolium p-toluenesulfonate, 1-ethyl-3-methylimidazolium methanesulfonate, 1,3-dimethylimidazolium dimethylphosphate, 1-ethyl-3-methylimidazolium thiocyanate, and 1-butyl-3-methylimidazolium dicyanamide, alone or as a mixture. Particularly preferred ionic liquids are 1-butyl-3-methylimidazolium bis(trifluoromethylsulfonyl)amide, 1-butyl-3-methylimidazolium iodide, and 1-butyl-3-methylimidazolium octylsulfate.

Supported Ionic Liquid-Phase (SILP) catalysts comprise an ionic liquid as disclosed above having the catalytically active complex dispersed on an inert support material having a large surface area. Said design allows the preparation of operationally solid catalysts which may be placed in the reactor bed while ensuring easy accessibility of the reactants to the active components of the catalyst in the ionic liquid. In the present context a SILP catalyst refers to a catalyst wherein the catalytically active component is dissolved/incorporated in the ionic liquid. Ideally a SILP catalyst utilizes the advantages of both homogeneous and heterogeneous catalysis. Thus the distance of diffusion is minimised since the ionic liquid is dispersed as a very thin film on a large surface area.

FIG. 1 shows diagrammatically the exemplary design of a SILP catalyst particle, wherein an immobilized catalytic ionic liquid phase consisting of ionic liquid $A^+B^-$ and a Group VIII metal represented as $M^+X^-$ is dispersed at low liquid loading on a porous high-area support. (By the term "low liquid loading" is meant the pore filling degree of an ionic liquid in the porous support. Typically the desired liquid loading is below 0.5.) Gaseous reactants diffuse into the porous structure of the SILP catalyst and reacts in the inter-phase of the thin ionic liquid catalyst film, where-after the product leaves the SILP particles again.

Suitable support materials are selected from the group consisting of silicas, polymers, zeolites, clays, alumina, titania, zirconia and combinations thereof. A preferred support material is silica, since it is mechanically robust, possesses a large surface area and is easy to process to the desired particle sizes.

The process according to the invention may be used for the carbonylation of any carbonylatable reactant. The term "carbonylatable reactant" as used in the present context is intended to mean any organic reactant which is capable of reacting with carbon monoxide, under carbonylation conditions of temperature and pressure, to obtain a reaction product resulting from the insertion of carbon monoxide into one or more chemical bonds. Examples of carbonylatable compounds include alcohols, ethers, and carboxylic acid esters having up to about 20 carbon atoms. More particularly said carbonylatable reactants are selected from the group consisting of saturated or mono- or diunsaturated, linear or branched aliphatic $C_1$-$C_{20}$ reactants and saturated or mono- or diunsaturated aromatic reactants having from 7 to 20 carbon atoms.

If the desired product of the carbonylation process is an acid or a derivative thereof, such as an ester or ether thereof, preferred carbonylatable reactants are alcohols, in particular lower alcohols. The most preferred alcohol is methanol, which is reacted with carbon monoxide to produce the industrially important chemical acetic acid.

In a preferred embodiment of the process according to the invention a reaction promoter is used. Suitable reaction promoters are selected from the group consisting of halides, hydrogen halides, or alkyl or aryl halides having up to about 10 carbon atoms. Preferred halides are selected from chlorine, bromine and iodine compounds, most preferably iodine compounds, that are gaseous under vapour phase carbonylation conditions. Suitable halides include hydrogen halides such as hydrogen iodide and gaseous hydroiodic acid; alkyl and aryl halides having up to about 10 carbon atoms such as methyl iodide, ethyl iodide, methyl bromide, ethyl bromide, benzyl iodide and any mixtures thereof. The halide may also be molecular halogen such as $I_2$, $Br_2$ or $Cl_2$. In the embodiment of the process according to the invention in which carbon monoxide is reacted with methanol to produce acetic acid, the most preferred reaction promoter is methyl iodide.

Scheme 1 below shows the essential steps of the catalytic cycle for the Monsanto carbonylation process of methanol for the preparation of acetic acid. Without wishing to be bound by any specific theory it is thought that the process according to the invention may be performed analogously for any carbonylatable reactant.

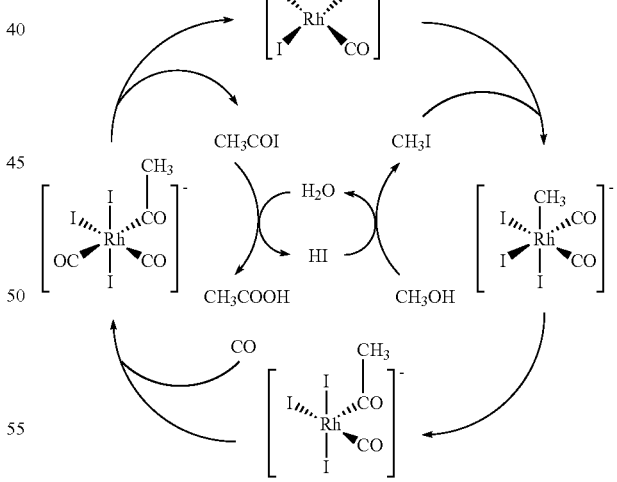

SCHEME 1

The reaction mechanism of the Monsanto process as it is believed to take place is thus as follows: Methanol is first reacted with an iodide source (HI) to form methyl iodide. Methyl iodide reacts with the rhodium complex by oxidative addition of methyl and iodide to the rhodium complex under formation of an alkyl complex. Said addition is followed by a migratory insertion of CO between the methyl group and the rhodium atom under formation of an unsaturated acyl complex having a free coordination site. Said "free" coordination site is occupied by a new CO molecule and subsequently acetic acid iodide is separated by reductive elimination of the acyl group and one of the iodide ligands. Acetic acid iodide is converted to acetic acid by reaction with water to reform the iodide source. Said iodide source is by re-reaction with methanol converted to the reaction promoter methyl iodide.

The carbonylation reaction according to the invention may be carried out at a temperature in the range from ambient to the temperature of decomposition of the ionic liquid at a pressure in the range 1-100 bar. However, since the carbonylation reaction is to take place in the gaseous phase the temperature must be kept above the dew point of the carbonylation reaction mixture. Typically the process according to the invention is carried out at a temperature in the range 100-300° C., more preferably in the range 150-230° C.

A wide range of pressures is available under which the carbonylation process according to the invention may be carried out provided maintenance of a gaseous state of all reactants is ensured. Typically the process according to the invention is carried out at a pressure in the range 5-50 bar, more preferably in the range 10-30 bar.

Figure 2:
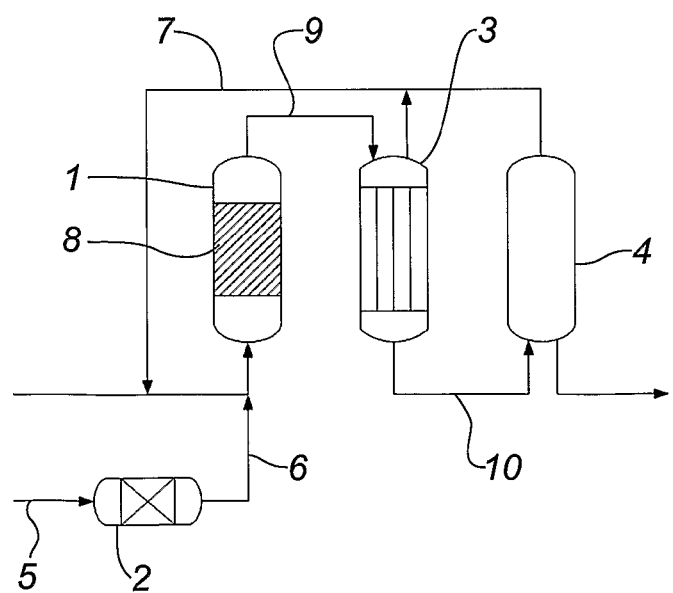
FIG. 2 is a flow-sheet showing diagrammatically the process according to the invention.

The process according to the invention may be carried out in an apparatus shown diagrammatically in FIG. 2, wherein said apparatus comprises:
i) at least one reactor 1;
ii) at least one liquid evaporator 2;
iii) at least one condenser 3;
iv) at least one separator 4 to separate the product stream from residual process gas which is recycled to said at least one reactor.

Through an evaporator inlet line 5 liquid carbonylatable reactant enters the evaporator 2. In a preferred embodiment of the invention a liquid mixture of carbonylatable reactant and reaction promoter, at any desired ratio, such as about 20:1-1:1, preferably about 9:1-2:1, enters the evaporator 2. The process gas is evaporated by the evaporator and combined with re-circulated process gas from line 7. The reactant gas mixture enters the reactor 1 through a reactor inlet line 6 either at the bottom as shown on FIG. 2 or at the top, if so desired. The reactor 1 to be used in the process according to the invention may be any conventional fixed-bed or fluidised-bed reactor, wherein the SILP catalyst is present. As an alternative to the above mentioned fixed-bed or fluidised-bed reactor a tube reactor may be employed. A single reactor may be used, however, the use of more than one reactor, in series or parallel, is also contemplated in the present invention.

The reaction mixture is forced to pass the SILP catalyst, wherein the presence of the very thin film of ionic liquid containing the catalyst dispersed on a robust, inert, porous high-area support material 8 offers a highly efficient use of the ionic liquid catalyst phase. The SILP catalyst thus requires smaller amounts of expensive metal catalyst and ionic liquid than any prior art catalyst systems. Due to the increased efficiency of the catalyst also a smaller reactor size may be used compared to prior art reaction designs in order to obtain similar catalyst efficiency. The heat of the exothermic reaction may be removed by inter-stage cooling of a multi-bed reactor, through the fluidised bed design or as an alternative using a tube reactor with external cooling.

The product stream from the reactor 1 is fed to a condenser 3 through a condenser inlet line 9 either at the top as shown on FIG. 2 or at the bottom thereof, if so desired. In the condenser 3 the gaseous reactants are evaporated from the top of the condenser 3 and re-circulated via line 7 to the reactor 1 whereas the liquified reaction products are transferred to a separator 4 through a liquid reaction product line 10. In the separator 4 a further separation of gaseous carbon monoxide and any other process gasses, if present, from the purified liquid product stream is obtained. The product stream from the separator 4 is processed further in a manner known per se employing e.g. fractional distillations and/or drying operations. The separator 4 may be any separator known in the art, such as a common distillation unit, a flash distillation unit etc.

In each of the above described process steps a single unit operation device will normally be used. However, the invention also contemplates the use of more than one unit operation device, such as e.g. more than one distillation unit, if required.

A major advantage by the use of the above simple process design is the omission of any catalyst recirculation since the catalyst is maintained in the reactor. Separation of the liquid phase currently employed in industrial plants often results in catalyst deactivation since carefully controlled conditions are required in order to avoid critical low pressures in connection with flash distillation operations. This also adds to a reduced demand for expensive catalyst material by the process according to the invention. Furthermore the simplified process design provides economical benefits as a result of lower operating and running costs. Existing plants may easily be adapted to the apparatus according to the invention or may be implemented at reduced plant investments.

EXAMPLES

The following examples illustrate the invention without limiting its scope or content.

SILP Catalyst Preparation

The 1-butyl-3-methylimidazolium iodide/dicarbonyldiiodorhodium(I) SILP catalyst employed in the examples was prepared by initial stirring of a dry methanol solution (8 ml) containing 16.5 mg tetracarbonyldiiododirhodium(I) (0.029 mmol) metal precursor and 302.5 mg ionic liquid 1-butyl-3-methylimidazolium iodide (1.137 mmol) under argon atmosphere for 24 hours. Subsequently, 0.600 g thermally pretreated (500° C., 15 h, in air) silica support (silica gel 100, Merck; BET surface area: 304 $m^2g^{-1}$; pore volume: 1.01 $cm^3g^{-1}$; mean pore diameter (monomodal): 13.2 nm) was added, where after the suspension was left with slow stirring for additionally 4 hours before the volatile solvent was removed at reduced pressure at room temperature. The residue consisting of fine red-brown SILP catalyst particles was then dried in a vacuum oven overnight (0.1 mbar, 60° C.) and further kept in vacuo over phosphor pentaoxide prior to use.

Catalytic Test System

Continuous, gas-phase carbonylations of methanol with carbon monoxide and methyl iodide as reaction promoter were performed in an all-heated stainless steel (AISI 316Ti) catalyst test system with the SILP catalyst positioned as a fixed-bed in a tubular reactor, placed in a temperature controlled aluminum block oven. The test system allowed the reactant feed composition to be controlled by gas- and liquid mass-flow controllers integrated with an evaporator and mixing unit and the reaction pressure to be controlled by a regulator valve equipped with a pneumatic actuator via connection to an electronic controller and pressure transducer. Gas-phase reactants and products were analyzed continuously by an integrated on-line FID-GC using auto gas sampling.

Example 1

1.00 g of SILP catalyst (containing 0.0437 mmol Rh metal), prepared as above, was positioned in a fixed catalyst bed in the tubular reactor where after the system was pressurized with carbon monoxide gas at a constant flow ($F_{CO}$) of 50 $ncm^3$ $min^{-1}$ to a constant reaction pressure ($P_r$) of 20 bara.

Meanwhile the reactor was heated to a constant reaction temperature ($T_r$) of 180° C. and the rest of the test system to 160° C. When the preset reaction pressure and temperatures were reached the carbon monoxide gas was bypassed the reactor, and a liquid mixture containing 75:25 w/w % of methanol:methyl iodide was introduced into the bypassed reactant gas, after evaporation of the liquid mixture, with a constant flow ($F_{liq}$) of 0.69 gh$^{-1}$. When the reactant gas mixture composition became constant, as determined by the FID-GC analysis, the methanol carbonylation reaction was started by allowing the reactant gas stream to flow through the SILP catalyst bed. The carbonylation reaction was afterwards followed for 1.5 hour while determining the gas composition regularly by FID-GC analysis, allowing determination of methanol conversion and catalyst activity (as turn-over-frequency in mol product formed per mol rhodium per hour) and selectivity for formation of the observed products acetic acid (AcOH), acetic acid methyl ester (AcOMe) and dimethyl-ether (MeOMe), respectively.

TABLE 1[a]

| Exp. No. | Time (h) | Conversion (%) | TOP (h$^{-1}$) | | | Product selectivity (%) | | |
|---|---|---|---|---|---|---|---|---|
| | | | AcOH | AcOMe | MeOMe | AcOH | AcOMe | MeOMe |
| 1.1 | 0.00 | 0.0 | 0.0 | 0.0 | 0.0 | 0.0 | 0.0 | 0.0 |
| 1.2 | 0.25 | 9.7 | 0.0 | 0.0 | 0.0 | 0.0 | 0.0 | 0.0 |
| 1.3 | 0.50 | 80.3 | 6.4 | 51.1 | 0.0 | 11.1 | 88.9 | 0.0 |
| 1.4 | 0.75 | 95.6 | 13.3 | 48.0 | 0.0 | 21.6 | 78.4 | 0.0 |
| 1.5 | 1.00 | 97.7 | 14.4 | 49.8 | 2.0 | 21.8 | 75.2 | 3.1 |
| 1.6 | 1.25 | 98.7 | 17.1 | 54.2 | 2.7 | 23.1 | 73.2 | 3.7 |
| 1.7 | 1.50 | 98.8 | 17.1 | 59.4 | 3.4 | 21.4 | 74.4 | 4.2 |

[a]Reaction conditions: $P_r$ = 20 bara, $T_r$ = 180° C., $F_{CO}$ = 50 ncm$^3$min$^{-1}$, $F_{liq}$ = 0.69 gh$^{-1}$.

Example 2

The results illustrated in this example are consecutive steady-state results obtained after continuation of the methanol carbonylation reaction described in Example 1 at 180° C., using the 1-butyl-37-methylimidazolium iodide/dicarbonyl-diiodorhodium (I) SILP catalyst, at different reaction pressure and reactant flows, respectively.

TABLE 2[b]

| Exp. No. | Time (h) | $P_r$ (bara) | $F_{CO}$ (ncm$^3$min$^{-1}$) | $F_{liq}$ (gh$^{-1}$) | AcOH | AcOMe | MeOMe |
|---|---|---|---|---|---|---|---|
| | | | | | TOP (h$^{-1}$) | | |
| 2.1 | 3.00 | 10 | 50 | 0.69 | 3.4 | 66.3 | 1.5 |
| 2.2 | 4.50 | 10 | 100 | 1.38 | 5.0 | 27.1 | 3.3 |
| | | | | | Product selectivity (%) | | |
| 2.1 | 3.00 | 10 | 50 | 0.69 | 4.7 | 93.1 | 2.2 |
| 2.2 | 4.50 | 10 | 100 | 1.38 | 14.1 | 76.7 | 9.2 |

[b]Reaction temperature $T_r$ = 180° C.

The invention claimed is:

1. A process for continuous carbonylation of carbonylatable products, comprising:
  reacting carbon monoxide in a gaseous phase with a carbonylatable reactant in a gaseous phase, and contacting the carbonylatable reactant and carbon monoxide with a Supported Ionic Liquid-Phase (SILP) catalyst comprising a solution of a Group VIII metal in an ionic liquid confined on a porous support to prepare a carboxylic acid or derivative thereof.

2. The process according to claim 1, wherein reacting comprises:
  continuously feeding the carbonylatable reactant and the carbon monoxide to a reaction zone;
  continuously contacting the carbonylatable reactant and carbon monoxide with the SILP catalyst; and
  continuously recovering from the reaction zone a gaseous effluent comprising a carbonylated product.

3. The process according to claim 2, further comprising adding a reaction promoter to the reaction zone.

4. The process according to claim 1, wherein the Group VIII metal is selected from the group consisting of iron, ruthenium, rhodium, iridium, nickel, cobalt, palladium and any combinations thereof.

5. The process according to claim 1, wherein the ionic liquid is represented by formula A$^+$B$^-$, in which A$^+$ represents a quaternary nitrogen- and/or a quaternary phosphorous-containing cation.

6. The process according to claim 5, wherein A$^+$ represents a cation selected from the group consisting of

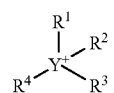

i)

wherein R$^1$, R$^2$, R$^3$, and R$^4$ are independently selected from optionally substituted, linear or branched-chained C$_1$-C$_{20}$ alkyl, optionally substituted cyclic C$_3$-C$_{20}$ alkyl, and optionally substituted C$_6$-C$_{20}$ aryl; and Y is N or P;

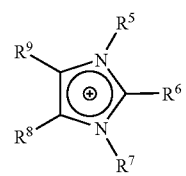

ii)

wherein R$^5$ and R$^7$ are independently selected from optionally substituted, linear or branched-chained C$_1$-C$_{20}$ alkyl, optionally substituted cyclic C$_3$-C$_{20}$ alkyl, and optionally substituted C$_6$-C$_{20}$ aryl; and R$^6$, R$^8$ and R$^9$ are independently selected from hydrogen, optionally substituted, linear or branched-chained C$_1$-C$_{20}$ alkyl, optionally substituted cyclic C$_3$-C$_{20}$ alkyl, and optionally substituted C$_6$-C$_{20}$ aryl;

iii)

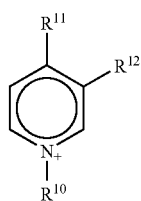

wherein $R^{19}$ is independently selected from optionally substituted, linear or branched -chained $C_1$-$C_{20}$ alkyl, optionally substituted cyclic $C_3$-$C_{20}$ alkyl, and optionally substituted $C_6$-$C_{20}$ aryl; and $R^{11}$ and $R^{12}$ are independently selected from hydrogen, optionally substituted, linear or branched-chained $C_1$-$C_{20}$ alkyl, optionally substituted cyclic $C_3$-$C_{20}$ alkyl, and optionally substituted $C_6$-$C_{20}$ aryl; and iv)

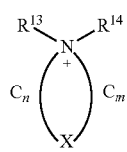

wherein $R^{13}$ and $R^{14}$ are independently selected from optionally substituted, linear or branched-chained $C_1$-$C_{20}$ alkyl, optionally substituted cyclic $C_3$-$C_{20}$ alkyl, and optionally substituted $C_6$-$C_{20}$ aryl; X is C, N, O, or S; n and m are each integers from 0 to 6 with the proviso that the sum $1 \leq m+n \leq 6$.

7. The process according to claim 5, wherein the anion B⁻ represents an anion selected from the group consisting of halides, nitrates, sulfates, sulfonates, sulfonyl amides, phosphates, borates, antimonates, and acetates or optionally halogen, hydroxyl and $C_1$-$C_6$ alkoxysubstituted hydrocarbyl derivatives thereof.

8. The process according to claim 1, wherein the ionic liquid is a composition selected from the group consisting of tetrabutylphosphonium tetrafluoroborate, N-butylpyridinium hexafluorophosphate, N-ethylpyridinium tetrafluoroborate, 1-butyl-1-methylpyrrolidinium bis(trifluoromethylsulfonyl)amide, 1-butyl-3-methylimidazolium tetrafluoroborate, 1-butyl-3-methylimidazolium hexafluorophosphate, 1-butyl-3-methylimidazolium trifluoromethylsulfonate, 1-butyl-3-methylimidazolium bis(trifluoromethylsulfonyl)amide, 1-ethyl-3-methylimidazolium bis(trifluoromethylsulfonyl)amide, 1-butyl-3-methylimidazolium acetate, 1-butyl-3-methylimidazolium iodide, 1-ethyl-3-methylimidazolium hydrogensulfate, 1-butyl-3-methylimidazolium methylsulfate, 1-ethyl-3-methylimidazolium ethylsulfate, 1-butyl-3-methylimidazolium octylsulfate, 1,3-dimethylimidazolium octylsulfate, 1-butyl-3-ethylimidazolium p-toluenesulfonate, 1-ethyl-3-methylimidazolium methanesulfonate, 1,3-dimethylimidazolium dimethylphosphate, 1-ethyl-3-methylimidazolium thiocyanate, and 1-butyl-3-methylimidazolium dicyanamide, in particular 1-butyl-3-methylimidazolium bis(trifluoromethylsulfonyl)amide, 1-butyl-3-methylimidazolium iodide, and 1-butyl-3-methylimidazolium octylsulfate, and mixtures thereof.

9. The process according to claim 1, wherein the support of is a material selected from the group consisting of silicas, polymers, zeolites, clays, alumina, titanic, zirconia and combinations thereof.

10. The process according to claim 2, wherein the carbonylatable reactant is a reactant selected from the group consisting of alcohols, ethers, and carboxylic acid esters having up to 20 carbon atoms.

11. The process according to claim 10, wherein the carbonylatable reactant is a reactant selected from the group consisting of saturated or mono- or di-unsaturated, linear or branched aliphatic $C_1$-$C_{20}$ reactants and saturated or mono- or di-unsaturated aromatic reactants having from 7 to 20 carbon atoms.

12. The process according to claim 10, wherein the reactant is an alcohol.

13. The process according to claim 12, wherein the alcohol is methanol.

14. The process according to claim 3, wherein the reaction promoter is selected from the group consisting of halides, hydrogen halides, and alkyl or aryl halides having up to about 10 carbon atoms.

15. The process according to claim 14, wherein the reaction promoter is methyl iodide.

16. The process according to claim 1, wherein the reacting is carried out at a temperature in a range from ambient to a temperature of decomposition of the ionic liquid at a pressure in the range 1-100 bar.

17. The process according to claim 16, wherein the reacting is carried out at a temperature in the range 100-300° C.

18. The process according to claim 16, wherein the reacting is carried out at a pressure in the range 5-50 bar.

19. The process according to claim 1, wherein the support is silica.

20. The process according to claim 16, wherein the reacting is carried out at a temperature in the 150-230° C.

21. The process according to claim 16, wherein the reacting is carried out at a pressure in the range 10-30 bar.

22. A process for continuous carbonylation of carbonylatable products, comprising:
diffusing carbon monoxide in a gaseous phase and a carbonylatable reactant in a gaseous phase through a porous support, the support comprising an Supported Ionic Liquid-Phase (SILP) catalyst disposed thereon in a film, the SILP catalyst comprising an ionic liquid and a Group VIII metal; and
reacting the carbon monoxide and the carbonylatable reactant in an inter-phase of the film to prepare a carboxylic acid or derivative thereof.

* * * * *